United States Patent [19]
Cutler et al.

[11] Patent Number: 5,922,889
[45] Date of Patent: Jul. 13, 1999

[54] SYNTHESIS OF ISOCHROMANS AND THEIR DERIVATIVES

[75] Inventors: Horace G. Cutler, Watkinsville; George Majetich, Athens; Xinrong Tian, Athens; Paul Spearing, Athens, all of Ga.

[73] Assignee: The United States od America as Represented by the Secretary of Agriculture, Washington, D.C.

[21] Appl. No.: 08/667,749

[22] Filed: Jun. 21, 1996

Related U.S. Application Data

[51] Int. Cl.$^6$ ............... C07D 311/04; C07D 311/06; C07D 311/22; A01N 43/16
[52] U.S. Cl. ............... 549/408; 549/409; 549/410; 504/292
[58] Field of Search ............... 549/408, 409, 549/410; 504/292

[56] References Cited

PUBLICATIONS

Majecich, G., "Recent Trends in the Use of Natural Products and Their Derivatives as Potential Pharmaceutical Agents", Symposia Abstract Form, Jun. 1996.

Cutler et al., "3, 7–Dimethyl–8–hydroxy–y–methoxy–isochroman from Pencillium corylophilum: Plant Growth Regulatory Activity", Agric. Biol. Chem., vol. 53(7), pp. 1975–1977 (1989).

Cutler et al., "Ruakuric Acid: A Natural Product from Aspergillus Fumigatus", Phytochemistry, vol. 00, No. 00, pp. 1–00, 1996.

Cox et al., "A New Isochroman Mycotoxin Isolated from Penicillium steckii", J. Agric. Food Chem., vol. 27 (1979).

Steyn et al., "The Synthesis of Ochratoxins A and B Metabolites of Aspergillus ochraceus Wilh", Tetrahedron, vol. 23, pp. 4449–4461 (1967).

Greene, Protective Groups in Organic Synthesis, pp. 88–92, 1991.

Ziegler et al., "Mild Method for the Esterification of Fatty Acids", Synthetic Communications, vol. 9(6), pp. 539–543 (1979).

Holton and Nelson, "A New Protecting Group for Phels: Phenylthiomethyl (PTM) Ethers", Synthetic Communications, vol. 10(12), pp. 911–914 (1980).

Deady et al., "Preparation of Some Chromans from 1,3–diaryloxy–propanes", J. Chem. Soc., pp. 2094–2095 (1963).

Primary Examiner—Ba K. Trinh
Attorney, Agent, or Firm—M. Howard Silverstein; John D. Fado; Gail E. Poulos

[57] ABSTRACT

Isochromans and their derivatives have been chemically synthesized. These compounds possess significant phytotoxic activity which may be used as a biodegradable contact herbicide. The synthetic method allows for economic production of these herbicides.

16 Claims, 2 Drawing Sheets

Scheme 2

SYNTHESIS OF ISOCHROMANS AND THEIR DERIVATIVES

BACKGROUND OF THE INVENTION

1. Field of the Invention

This invention relates to novel, biologically active derivatives of isochromans, a synthetic method for preparing isochromans and their derivatives, especially 3,7-dimethyl-8-hydroxy-6-methxoyisochroman, 3,7-dimethyl-6-hydroxy-8-methoxyisochroman and their ether and ester derivatives; and to their use as an herbicide.

2. Description of the Prior Art

Cutler et al (Agric. Biol. Chem., Volume 53 (7), 1975–1977, 1989) report that the bulk culture of *Penicillium coryphilum* Dierckx (ATCC accession numbers 64543 and 64869) through solid fermentation, followed by extraction, led to the isolation of 3,7-dimethyl-8-hydroxy-6-methoxyisochroman(DHMI). This metabolite inhibits growth of etiolated wheat coleoptiles. Earlier, DHMI was reported to have been isolated from moldy millet hay implicated in the death of cattle (Cox et al, J. Agric. Food Chem., Volume 27, 999, 1979), but the metabolite was not tested in plants. Because DHMI has a functional hydroxyl group at C8, the acetate and methoxy derivatives were synthesized to determine if the free hydroxyl is necessary for biological activity toward plants. Cutler et al (supra) report that the parent compound, DHMI, significantly inhibits etiolated wheat coleoptile growth by 100% and 43%, respectively at $10^{-3}$ and $10^{-4}$M while DHMI-acetoxy inhibits it by 100% and 42%, respectively. Based on these results, the parent and two derivatives, initially obtained were assayed on greenhouse-grown bean, corn and tobacco plants. The methoxy derivative exhibited the most herbicidal activity in all plants, while the parent and acetoxy derivative were only active against corn.

Currently, DHMI is only available by fermentation of microorganisms that produce it. It would be desirable to be able to chemically synthesize DHMI and active derivatives in order to make their use as an herbicide economically feasible. The present invention provides a synthetic method for the preparation of 3,7-dimethyl-8-hydroxy-6-methoxyisochroman, the 3,7-dimethyl-6-hydroxy-8-methoxy isomer and their esters and ethers.

SUMMARY OF THE INVENTION

It is therefore an object of the present invention to provide novel isochroman compounds and their derivatives which have phytotoxic activity and a method for preparing them.

A further object of the present invention is to provide a method for synthesizing 3,7-dimethyl-8-hydroxy-6-methoxyisochroman, the 3,7-dimethyl-6-hydroxy-8-methoxy isomer, and their esters and ethers.

A still further object of the present invention is to provide a method for controlling plant growth of a plant or a seed using herbicidally effective amounts of isochromans and their derivatives.

Further objects and advantages of the present invention will become apparent from the following description.

DETAILED DESCRIPTION OF THE INVENTION

Figure 1:
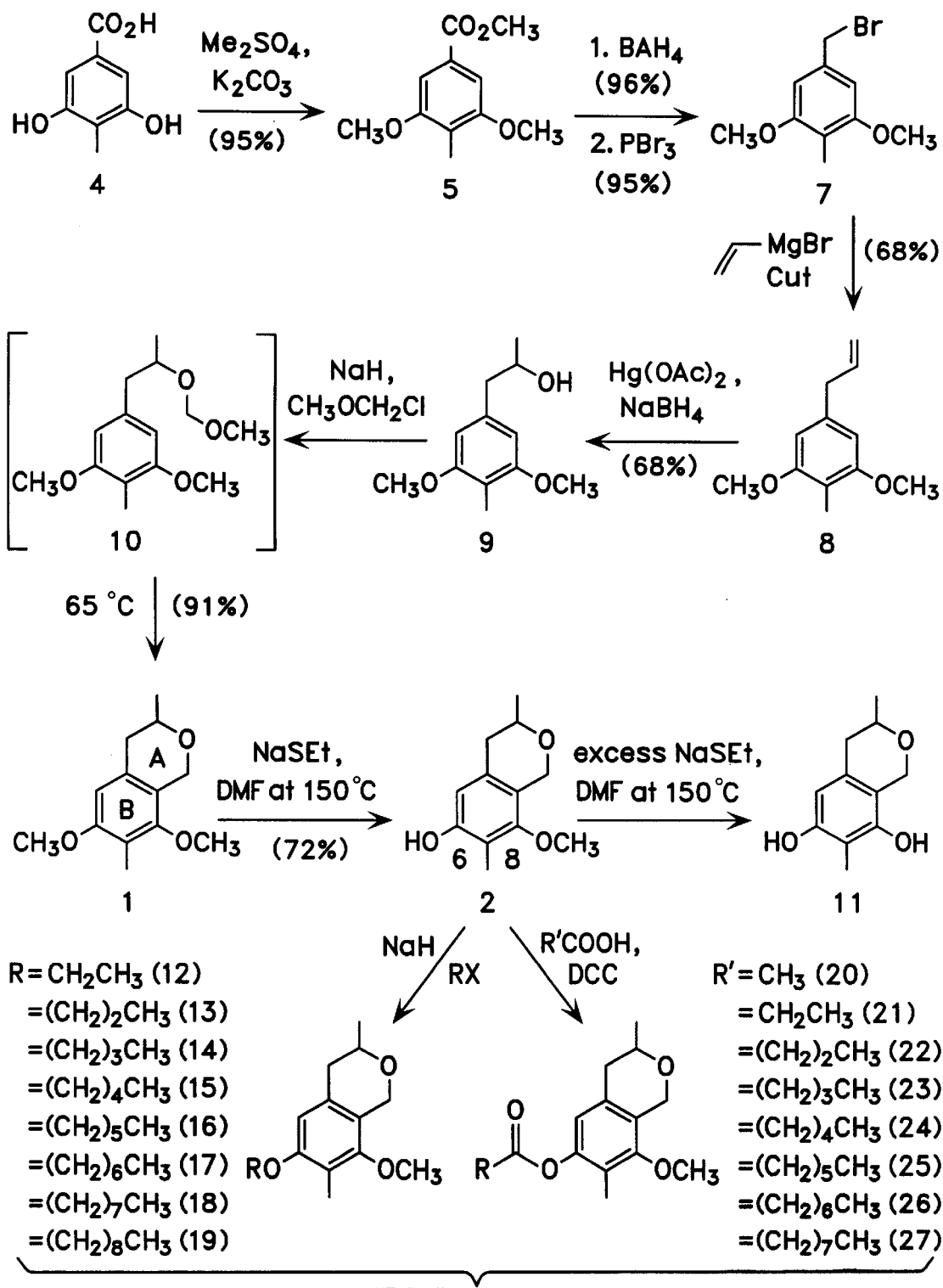
FIG. 1 is scheme 1 for the synthesis of 3,7-dimethoxyisochroman 1,3,7-dimethyl-6-hydroxy-8-methoxyisochroman, and derivatives.

The search for new compounds possessing useful biological activities requires that the new compounds and known compounds, especially natural products and their derivatives, be synthetically prepared. Synthetic preparation of natural compounds allows economical use of these products. The process of the invention is a synthetic method for the preparation of isochromans and their derivatives. Chromans are rare structures among the secondary metabolites of fungi. 3,7-Dimethyl-8-hydroxy-6-methoxyisochroman has been isolated from *Penicillium stecki* (Cox et al, J. Agric. Food Chem., Volume 27, 999, 1979). The isochromanones, 6,8-dihydroxy-1-methylisochroman-3-one, dihydrofuscin and deoxydihydrofucin and 6,8-dihydroxy-5-(3'-methylbut-2'-enyl)-1-methylisochroman-3-one have all been isolated from an unidentified fungus (Crawley, J. Chem. Soc., Perkin Trans. I, 221, 1981). Dihydrofuscin has also been found in *Oidiodendron fuscum* (Michael, Biochem. J., Volume 43, 528, 1948). Diplosporin (=diplodiol) (5s,6x)6-ethyl-5-hydroxy-3-hydroxymethyl-5,6,7,8-tetrahydrobenzo[b]pyran-4-one (Chalmlers et al, S. Afr. J. Chem., Volume 31, 111, 1978) {diploidiol, trans-6-ethyl-5-hydroxy-3-hydroxymethyl-5,6,7,8-tetrahydrochromane (Cutler et al, J. Agric. Food Chem., Volume 28, 135, 1980)} has been isolated from *Diploidia macrospora* and has an $LD_{50}$ of 88 mg $kg^{-1}$ against 1-day old chicks (Cutler et al, 1980, supra). 5-Deoxydiplosporin has also been isolated from *D. macrospora* (Chalmers et al, J. Chem. Soc., Perkin Trans. Volume 1, 148, 1979). Other chroman relatives include the chromene series, 2,2-dimethylchromene from *Lactarius picinus*. Furthermore, 6-methoxy-2,2-dimethylchromene; 8,8'-bis(6-methoxy-2,2-dimethylchromene; 6-methoxy-8[2'-methoxy-4'(3'-methyl-2'-butenyl)phenoxy]2,2-dimethylchromene; 6-methoxy-8[6'-hydroxy-2'-methoxy-4' (3'-methyl-2"-butenyl)phenyl]2,2-dimethylchromene; and hydroxy-methoxy-2,2-dimethylchromene have all been isolated from *L. picinus* and *L. fuliginosus* (Conca et al, Tetrahedron Letters, Volume 22, 4327, 1981). Ruakuric acid (6-acetyl-5-hydroxy-4-methoxy-chroman-2-carboxylic acid) has been isolated from *Aspergillus fumigatus* and does not exhibit biological activity in the etiolated wheat coleoptile assay (Cutler et al, unpublished).

The term isochroman refers to any compound containing the basic structure of a saturated six-member ring containing an oxygen and with an alkyl group ($R_1$) which can be any number of carbons, branched or straight chain, attached to the carbon atom at position 3 and a benzene ring with an alkyl group ($R_4$) which can be any number of carbons, branched or straight chains, attached to the carbon atom at position 7 as shown below:

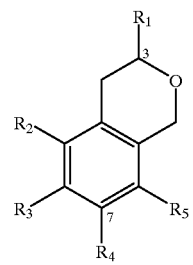

The oxygen atom can be in position 1, 2 or 4 of the saturated 6-member ring. $R_2$, $R_3$ and $R_5$ are either H (hydrogen), OH (hydroxyl), $OR_5$ wherein $R_5$ is a $C_1$ to $C_{10}$ alkyl group optionally containing olefinic, acetylenic or aryl moieties or R$_6$CO wherein R$_6$ is a C$_1$ to C$_{10}$ alkyl group.

It has now been discovered that a natural product, isochroman, and its derivatives which exhibit herbicidal activity can be synthesized with good yields. The synthesis of isochroman 1 (FIG. 1) begins with 3,5-dihydroxy-4-methyl benzoic acid which is exhaustively methylated to provide an ester 5 (FIG. 1). Known acid 4 can be purchased or prepared by any known method, such as for example, nitration of toluic acid followed by reduction of the 2 nitro groups, followed by diazoniation which gives 3,5-dihydroxy-4-methyl benzoic acid (4). Reduction of ester 5 with LiAlH$_4$ furnishes benzylic alcohol 6 (not shown). The OH group is then converted into a leaving group. A bromide leaving group, such as for example PBr$_3$ is preferred. Therefore, bromination of the benzylic alcohol with PBr$_3$ furnishes bromide 7 in approximately 91% overall yield. Subsequent treatment of bromide 7 with vinylmagnesium bromide or vinyllithium in the presence of a catalytic amount of a copper (I) catalyst, such as for example, Copper (I) iodide, produces olefin 8 in approximately 68% yield. Oxymercuration-demercuration of 8 gives secondary alcohol 9 in approximately 68% yield along with some unreacted starting material. Treatment of 9 with sodium hydride and chloromethyl ether in refluxing tetrahydrofuran generated methoxymethyl ether in situ (cf. 10), followed by cyclization to produce isochroman 1 in a 91% yield. While Lewis acid-catalyzed cyclialkylations (Brunson et al, J. Am. Chem. Soc., Volume 62, 36, 1940) have been used to synthesize chroman (Deady et al, J. Chem. Soc., 2094, 1963) and ochratoxin A37 (Steyn et al, Tetrahedron, Volume 23, 4449, 1967), the cyclization of 10 to 1, in the present invention, occurs under thermal conditions without a Lewis acid catalyst.

With the practical synthesis of isochroman 1, this compound can be selectively demethylated to produce 3,7-dimethyl-6-hydroxy-8-methoxyisochroman 2 and 3,7-dimethyl-8-hydroxy-6-methoxyisochroman 3 and their derivatives. Methylphenyl ethers can be easily deprotected using strong mineral acid (Greene et al, in "Protective Groups in Organic Synthesis, 2nd Edition, Wiley & Sons, New York page 145, 1991) or TMS-I (Jung et al, J. Org. Chem., Volume 42, 3761, 1977). However, it is a concern that acidic agents would compromise the A ring of the isochroman (cf. 1, FIG. 1). Therefore, nucleophilic reagents, such as sodium ethyl thiolate (NaSEt) or hydride reagents (Greene et al, supra) are used to effect deprotection (Feutrill et al, Tetrahedron Lett., 1327, 1970). The treatment of 1 with excess NaSEt in refluxing DMF gives only isochroman 2 in approximately 72% yield whereby the sterically less-hindered C6 methoxy group is selectively demethylated. With this practical synthesis, ester derivatives 20–27 are prepared without complications using a known procedure (Ziegler et al, Synth. Commun., Volume 9, 539, 1979) whereas ethers 12–19 are prepared using classical Williamson ether synthesis conditions.

Figure 2:
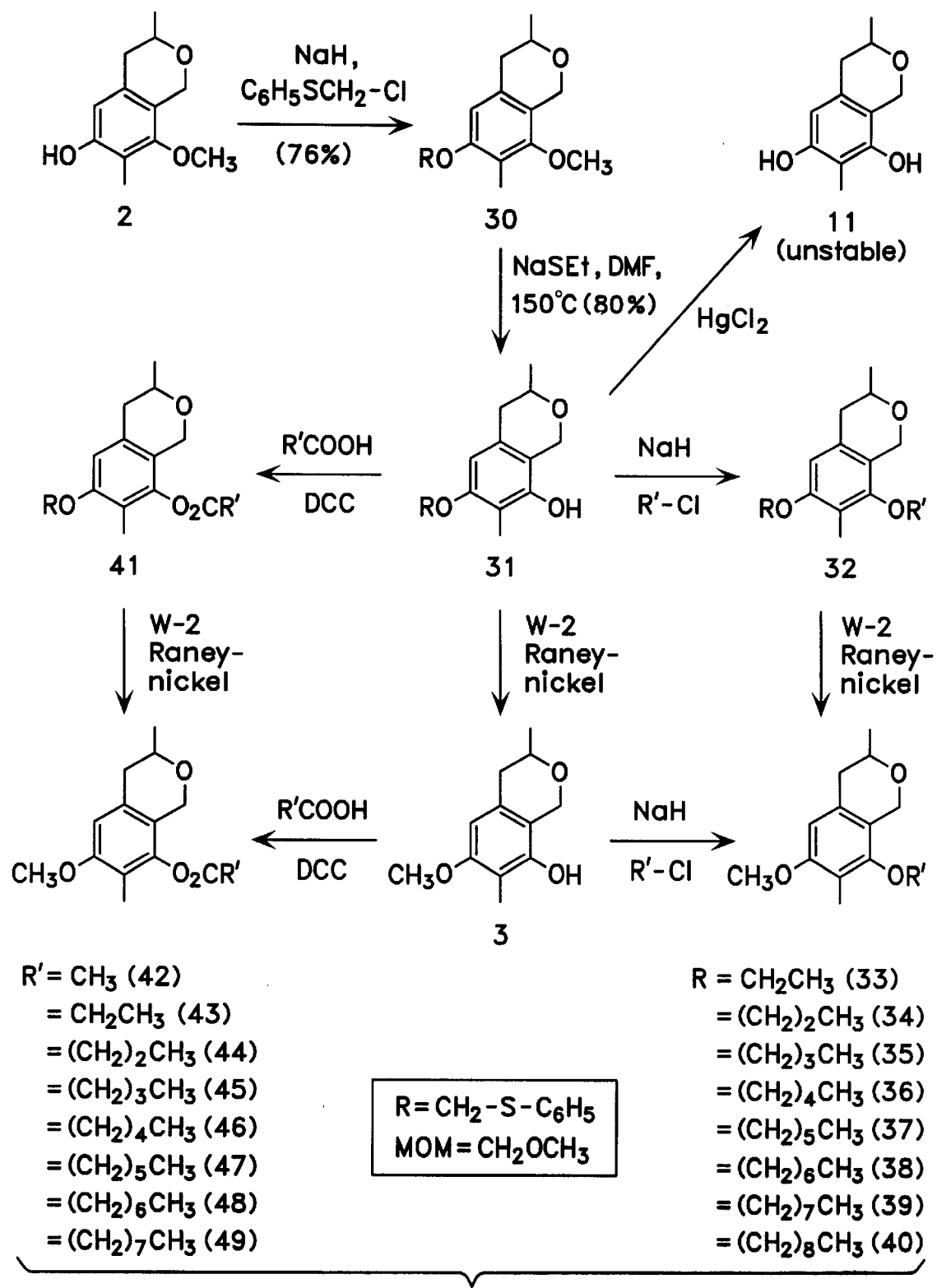
FIG. 2 is scheme 2 for the synthesis of 3,7-dimethyl-8-hydroxy-6-methoxyisochroman and derivatives.

To prepare isochroman 3, isochroman 2 is protected as a phenylmethyl ether 30 (FIG. 2). Treatment of 30 with sodium ethyl thiolate selectively removes the C(8)-methyl ether leaving the C(6) phenylmethyl ether intact (cf. 31, FIG. 2). 31 is desulfurized with W-2 Raney-nickel to convert the phenylthiomethyl ether protecting group into a methoxy ether, forming 3,7-dimethoxy-8-hydroxy-6-methoxyisochroman 3. Ether derivatives 32–39 of 3 are prepared by alkylating prior to desulfurization of the phenylthiomethyl ether group, i.e. 31 32 33–40.

Ester derivatives of 2 or 3 are prepared by mixing 2 or 3 with DCC and a straight chain or branched aliphatic acid, their unsaturated or hydroxylated derivatives having 1 to 10 carbon atoms. In theory, esters 42 through 50 could be prepared from either substrates 3 or 41 as shown in FIG. 2. In practice, however, the sequence 31 3 42–49 was employed because it required the preparation of fewer intermediates. Finally, hydrolysis of 31 using vigorous conditions [mercuric chloride in refluxing approxmately 4:1 acetonitrile:water] (Holton et al, Synth. Commun., Volume 10, 911, 1980) generates 6,8-dihydro-3,7-dimethylisochroman 11 which unfortunately decomposes under the reaction conditions.

Ether derivatives are prepared by mixing isochromans 2 or 3 with NaH and a halogenated alkane having 1 to 10 carbon atoms.

Isochromans and their derivatives are applied as herbicides in conjunction with a suitable solid or liquid inert carrier or vehicle as known in the art. Of particular interest are those which are agronomically acceptable. Alcohols, ketones, esters and aqueous surfactant mixtures are illustrative of suitable liquid carriers. The compound may also be formulated with solid inert carriers, such as talc, clay or vermiculite, or incorporated into conventional controlled release microparticles or microcapsules. Depending on the substrate, target species, mode of application and type of response desired, the concentration of active ingredient should be at least about 2% to about 10%. Factors such as phytotoxicity toward the target plant and tolerance of non-target species can be used by the skilled artisan in determining optimal level.

Isochromans act as herbicides by inhibiting or preventing growth or inducing mortality of the target plant or seed. The isochromans and their derivatives are biodegradable. The compound is administered in an amount effective to induce the desired response as predetermined by routine testing. Where the ultimate response is control of plant growth, an effective amount or herbicidally effective amount is defined to mean those quantities of agent which will result in a significant inhibition or prevention of growth of a test group as compared to an untreated group. Without being limited thereto, it is envisioned that application rates of approximately 1 to 2 pounds or more of isochromans per acre will be effective. However, the actual effective amount will of course vary with the species of plant, stage of development, the nature of the substrate, the type of vehicle or carrier, the period of treatment and other related factors.

To be effective, isochromans and their derivatives can be directly applied to plants or seeds, or the compound can be applied to the locus or the vicinity of, the plant or seed to be controlled. Compositions of the compound will typically be applied by spraying although solid formulations may be applied by dusting.

Isochromans and their derivatives are effective in controlling growth of a variety of plants. Without being limited thereto, these compounds are particularly effective against monocotyledonous plants and some dicotyledonous plants, including grasses, tobacco, beans, wheat and corn.

The following examples illustrate the invention using the preparation of 3,7-dimethyl-6-hydroxy-8-methoxyisochroman and 3,7-dimethyl-8-hydroxy-6-methoxyisochroman and their derivatives. They are intended to further illustrate the invention and are not intended to limit the scope as defined by the claims.

All reactions are run under an inert atmosphere of nitrogen and monitored by TLC analysis until the starting material is completely consumed. Proton NMR spectra is obtained in CDCl$_3$ and are calibrated using trace CHCl$_3$ present (δ7.26) as an internal reference.

EXAMPLE 1

To prepare methyl 3,5-dimethoxy-4-methylbenzoate (5) a solution of approximately 3.9 grams of 3,5-dihydroxy-4-methylbenzoic acid (4) in approximately 50 ml of acetone is added to approximately 21.3 grams $K_2CO_3$ and approximately 15.6 ml dimethyl sulfate and the mixture is refluxed for approximately 18 hours (FIG. 1). The resulting mixture is acidified with approximately 10% HCl and extracted with approximately 25 ml ether three times. The combined extracts are washed with brine, i.e. saturated salt water, dried over anhydrous $MgSO_4$ and concentrated to yield approximately 4.40 grams of 5, at an approximately 95% yield, which is homogeneous based of TLC analysis. [hexane:ether, 5:1. $R_f$ 5=0.44] a light brown solid: mp approximately 100.5–102° C.; $^1H$ NMR (250 MHz) δ 2.13 (s, 3H), 3.88 (s, 6H), 3.92 (s, 3H) 7.23 (s, 2H); $^{13}C$ NMR (62.5 MHz) 178.1, 157.9, 128.1, 120.2, 104.5, 55.7, 52.0, 8.5 ppm; IR (neat) 1713, 1142 $cm^{-1}$; ESI-MS (m/z) 211 ($MH^+$) (FIG. 1).

EXAMPLE 2

To prepare 3,5-dimethoxy-4-methylphenylmethyl alcohol (6) approximately 1.0 grams $LiAlH_4$ is slowly added to a solution of approximately 4.40 grams of methyl 3,5-dimethoxy-4-methylbenzoate (5) in approximately 150 ml ether at approximately 0° C. The mixture is stirred for about two hours, then quenched with saturated $NH_4Cl$. The following is a standard ethereal workup used throughout the examples. The aqueous phase organic solvent is removed under reduced pressure on a rotary evaporator and the residue is taken up in ether, washed with brine and dried over anhydrous $MgSO_4$. Filtration, followed by concentration at reduced pressure on a rotary evaporator and at approximately 1 torr to constant weight affords a crude residue which is purified by flash chromatography using NM silica gel 60 (230–400 mesh ASTM) and distilled reagent grade hexane:ether, approximately 4:1, gives approximately 3.63 grams of alcohol 6 at a yield of approximately 96% which is homogenous based on TLC analysis [hexane:ether, 1:1, $R_f$ 6=0.26] as a white solid: mp approximately 67.5–69° C.; $^1H$ NMR (250 MHz) δ 1.77 (t, 1 h, J=5.9 Hz), 2.09 (s, 3H), 3.83 (s, 6H), 4.65 (d, 2H, J=5.9 Hz), 6.56 (s, 2H); $^{13}C$ NMR (62.5 MHz) 158.3, 139.3, 113.6, 102.1, 65.7, 55.6, 8.0 ppm; IR (neat) 3250–3600, 1138 $cm^{-1}$; ESI-MS (m/z) 183 ($MH^+$) (FIG. 1).

EXAMPLE 3

To prepare 3,5-dimethoxy-4-methylphenylmethyl bromide (7), approximately 2.25 ml of $PBr_3$ is added to a solution of approximately 3.60 grams of 3,5-dimethoxy-4-methylphenylmethyl alcohol (6) in approximately 60 ml of ether at approximately 0° C. After about 2 hours the reaction is quenched with ice. Standard ethereal workup described in example 2 above, followed by chromatography of the residue (elution with hexanes:ether, approximately 4:1), gives approximately 4.60 grams of benzyl bromide 7 at a yield of approximately 95% which is homogeneous based on TLC analysis [hexanes:ether,approximately 2:1, $R_f$ 7=0.86] as a white crystalline solid: mp approximately 88–90° C.; $^1H$ NMR (250 MHz) δ 2.08 (s, 3H), 3.84 (s, 6H), 4.50 (s, 2H), 6.57 (s, 2H); $^{13}C$ NMR (62.5 MHz) 158.2, 135.8, 114.9, 104.1, 55.6, 34.6, 8.1 ppm; IR (neat) 1591, 1142 $cm^{-1}$; EI-MS (m/z) (relative density) 246 (10), 165 (100), 150 (10), 120 (11), 105 (8), 91 (22), 77 (20), 51 (15) (FIG. 1).

EXAMPLE 4

To prepare 1,3-dimethoxy-2-methyl-5-[2-propenyl]-benzene (8), an approximately 1.0M solution of vinylmagnesium bromide in approximately 28.2 ml THF is added to a stirred suspension of approximately 0.53 grams CuI in approximately 40 ml THF at about −40° C. and stirred for about 10 minutes. Approximately 2.3 grams of 3,5-dimethoxy-4-methylphenylmethyl bromide (7) is then added and the mixture is stirred at approximately −25° C. for approximately 2.5 hours. The standard ethereal workup (Example 2 above), followed by chromatography of the reside (elution with hexanes, gives approximately 1.23 grams of adduct 8 in a yield of approximately 68% which is homogenous based on TLC analysis [hexane:ether, approximately 10:1, $R_f$ 8=0.82] as a yellow oil: $^1H$ NMR (250 MHz) δ 2.09 (s, 3H), 3.38 (d, 2H, J=6.7 Hz), 3.83 (s, 6H), 5.08–5.18 (m, 2H), 5.91–6.05 (m, 1H), 6.40 (s, 2H); $^{13}C$ NMR (62.5 MHz) 158.2, 138.4, 137.4, 125.5, 115.7, 103.8, 55.6, 30.2, 7.9 ppm; IR (neat) 1588, 1109 $cm^{-1}$; ESI-MS (m/z) 193 ($MH^+$) (FIG. 1).

EXAMPLE 5

To prepare 1-[3,5-dimethoxy-4-methylphenyl]-propan-2-ol (9), approximately 1.23 grams of 1,3-dimethoxy-2-methyl-5-[2-propenyl]-benzene (8) in approximately 10 ml of THF is added to a solution of approximately 2.04 grams of $Hg(OAc)_2$ in approximately 30 ml of THF and approximately 15 ml of $H_2O$ at room temperature. The mixture is stirred until the yellow color fades (approximately 20 minutes) then it is cooled to approximately 0° C. and approximately 0.63 grams of $NaBH_4$ in approximately 10 ml THF is added. After approximately 20 minutes, the solution is saturated with NaCl and extracted about five times with approximately 20 ml ether. The combined ethereal extracts are dried over anhydrous $MgSO_4$, concentrated and the residue chromatographed (elution with hexane:ether, approximately 3:2) to yield approximately 0.92 grams of alcohol 9 at a yield of approximately 86%, based on recovery of approximately 0.25 grams of 8, which is homogeneous based on TLC analysis [hexanes:ether, approximately 1:1, $R_f$ 9=0.31] as a white crystalline solid: mp approximately 68–69° C.; $^1H$ NMR (250 MHz) δ 1.26 (d, 3H, J=6.0 Hz), 1.76 (s, 1H), 2.07 (s, 3H), 2.57–2.81 (m, 2H), 3.82 (s, 6H), 3.98–4.08 (m, 1H0, 6.40 (s, 2H); $^{13}C$ NMR (62.5 MHz) 158.2, 136.7, 112.4, 104.4, 68.8, 55.6, 46.2, 22.7, 7.9 ppm; IR (neat) 3300–350, 1587, 1101 $cm^{-1}$; ESI-MS (m/z) 211 ($MH^+$) (FIG. 1).

EXAMPLE 6

To prepare 6,8-dimethoxy-3,7-dimethylisochroman (1), approximately 3.89 grams of 1-[3,5-dimethoxy-4-methylphenyl]-propan-2-ol (9) in approximately 50 ml THF is added to astirred suspension of approximately 1.85 grams, approximately 46.3 mmol of approximately 60% dispersion in mineral oil, at about room temperature and is stirred for about 45 minutes. approximately 3.52 ml of chloromethyl methyl ether is added and the solution is heated to about 65° C. for approximately 2 hours. The standard ethereal workup, example 2 above, is followed by chromatography (elution with heane:ether, approximately 5:1) and gives approximately 3.74 grams of isochroman 1 in a yield of approximately 91% which is homogeneous based on TLC analysis [hexane:ether, approximately 4:1, $R_f$ 1=0.51] as a white crystalline solid: mp approximately 52.5–54° C.; $^1H$ NMR (250 MHz) δ 1.35 (d, 3H, J=6.0 Hz), 2.12 (s, 3H), 2.65 (d, 2H, J=6.7 Hz), 3.69 (s, 3H), 3.80 (S, 6H), 4.70 (D, 1H, J=15.1 Hz), 4.93 (d, 1H, J=15.1 Hz), 6.39 (s, 1H); $^{13}C$ NMR (62.5 MHz) 154.7, 133.8, 132.2, 119.9, 116.9, 106.0, 70.5, 64.5, 60.1, 55.5, 35.8, 21.5, 8.5 ppm; IR (neat) 1608, 1456, 1121 $cm^{-1}$; ESI-MS (m/z) 223 ($MH^+$) (FIG. 1).

EXAMPLE 7

To prepare 3,7-dimethyl-6-hydroxy-8-methoxyisochroman (2), approximately 21.0 ml of ethanethiol is added to a stirred suspension of approximately 17.0 grams of NaH, approximately 425 mmol of an approximately 60% dispersion in mineral oil, in approximately 150 ml DMF at about 0° C., then stirred for about 1 hour at about room temperature. Approximately 3.15 grams of isochroman 1 is added to the reaction mixture and the resulting mixture heated to about 130° C. for about 6 hours. The reaction is quenched with saturated $NH_4Cl$, acidified with approximately 10% HCl, saturated with NaCl and then extracted about five times with approximately 40 ml of ether. The combined organic layers are washed with brine, then stirred vigorously with approximately 50.0 grams of $CuSO_4$ for about 1 hour. The solids are filtered and the filtrate concentrated. The resulting residue is chromatographed (hexane:ether, approximately 2:1) and gave approximately 2.12 grams of phenol 2 at a yield of approximately 72% which is homogeneous based on TLC analysis [hexane:ether, approximately 1:1, $R_f$ 2=0.56] as a white crystalline solid: mp approximately 149.5–151° C.; $^1$H NMR (250 MHz) δ 1.34 (d, 3H, J=6.0 Hz), 2.07 (s, 3H), 2.63 (d, 2H, J=5.9 Hz), 3.71–3.82 (m, 1H), 3.79 (s, 3H), 4.65 (d, 3H, J=14.8 Hz), 4.67 (s, 1H), 4.92 (d, 1H, J=14.8 Hz), 6.23 (s, 1H); $^{13}$C NM (62.5 MHz) 156.4, 149.9, 132.2, 114.1, 108.3, 102.7, 70.4, 64.3, 55.5, 35.8, 21.4, 7.5 ppm; IR (neat) 3150–3500, 1591, 1126 cm$^{-1}$; ESI-MS (m/z) 209 (MH$^+$) (FIG. 1).

EXAMPLE 8

To prepare 3,7-dimethyl-6-(ethoxy)8-methoxyisochroman (12), approximately 80 mg of isochroman 2 is added to a stirred suspension of approximately 18 mg of NaH, approximately 0.46 mmol of an approximately 60% dispersion in mineral oil, in approximately 0.5 ml mineral oil at about 0° C. After stirring at about room temperature for about 30 minutes, about 37 ul iodoethane is added and the mixture is stirred for about a 90 minute period. The reaction is quenched with saturated $NH_4Cl$ and extracted about 3 times with approximately 5 ml of ether. The combined ethereal extracts are washed with approximately 10% $CuSO_4$ and brine, then dried over anhydrous $MgSO_4$ and concentrated. The residue is chrmatographed (elution with hexane:ether, approximately 5:1), to give approximately 79 mg of ether 12, at an approximately 87% yield, as a white crystalline solid: $R_f$ 12=0.08 (hexane:ether, approximately 1:1); mp approximately 75–76.5° C.; $^1$H NMR (250 MHz) δ 1.34 (d, 3H, J=6.1 Hz), 1.39 (t, 3H, J=7.2 Hz), 2.11 (s, 3H), 2.64 (d, 2H, J=6.7 Hz), 3.68–3.85 (m, 3H), 3.79 (s, 3H), 4.69 (d, 1H, J=7.2 Hz), 4.94 (d, 1H, J=15.1 Hz), 6.38 (s, 1H); $^{13}$C NMR (62.5 MHz) 157.0, 153.9, 132.0, 120.1, 117.1, 105.8, 70.5, 68.3, 64.7, 55.4, 35.8, 21.5, 15.6, 8.8 ppm; IR (neat) 1609, 1124 cm$^{-1}$; ESI-MS (m/z) 237 (MH$^+$) (FIG. 1).

EXAMPLE 9

To prepare 3,7-dimethyl-8-methoxy-6-propoxyisochroman (13), isochroman 2 is reacted with 1-bromopropane (cf. the preparation of 12, example 8 above) in approximately 76% yield as a white crystalline solid: $R_f$ 13=0.80 (hexane:ether, approximately 1:1); mp approximately 53–54° C.; $^1$H NMR (250 MHz) δ 1.05 (t, 3H, J=7.4 Hz), 1.34 (d, 3H, J=6.4 Hz), 1.79 (sextet, 2H, J=7.0 Hz), 2.10 (s, 3H), 2.65 (d, 3H, J=6.8 Hz), 3.69 (t, 2H, J=6.6 Hz), 3.69–3.80 (m, 1H), 3.79 (s, 3H), 4.69 (d, 1H, J=14.9 Hz), 4.95 (d, 1H, J=14.9 Hz), 6.38 (s, 1H); $^{13}$C NMR (62.5 MHz) 157.1, 153.9, 132.0, 120.0, 117.1, 105.8, 74.3, 70.5, 64.7, 55.4, 35.8, 23.5, 21.5, 10.5, 8.8 ppm; IR (neat) 1609, 1122 cm$^{-1}$; ESI-MS (m/z) 251 (MH$^+$) (FIG. 1).

EXAMPLE 10

To prepare 6-butoxy-3,7-dimethyl-8-methoxyisochroman (14), Isochroman 2 is reacted with 1-bromobutane (cf. The preparation of 12, example 8 above) in approximately 86% yield as a colorless oil: $R_f$ 14=0.82 (hexane:ether, approximately 1:1); $^1$H NMR (250 MHz) δ 0.95 (t, 3H, J=7.0 Hz), 1.35 (d, 3H, J=6.0 Hz), 1.37–1.45 (m, 4H), 1.71–1.80 (m, 2H), 2.11 (s, 3H), 2.64 (d, 2H, J=6.6 Hz), 3.70 (t, 2H, J=6.6 Hz), 3.69–3.80 (m, 1H), 3.79 (s, 3H), 4.69 (d, 1H, J=15.0 Hz), 4.95 (d, 1H, J=15.0 Hz), 6.37 (s, 1H); $^{13}$C NMR (62.5 MHz) 157.1, 153.9, 132.0, 120.0, 117.1, 105.8, 72.8, 70.5, 64.7, 55.4, 35.8, 29.9, 28.1, 22.5, 21.5, 14.0, 8.8 ppm; IR (neat) 1609, 1465, 1125 cm$^{-1}$; ESI-MS (m/z) 279 (MH$^+$) (FIG. 1).

EXAMPLE 11

To prepare 3,7-dimethyl-8-methoxy-6-pentanoxyisochroman (15), isochroman 2 is reacted with 1-bromopentane (cf. The preparation of 12, example 8 above) in approximately 89% yield as a colorless oil: $R_f$ 14=0.82 (hexane:ether, approximately 1:1); $^1$H NMR (250 MHz) δ 0.95 (t, 3H, J=7.0 Hz), 1.35 (d, 3H, J=6.0 Hz), 1.37–1.45 (m, 4H), 1.71–1.80 (m, 2H), 2.11 (s, 3H), 2.64 (d, 2H, J=6.6 Hz), 3.70 (t, 2H, J=6.6 Hz), 3.69–3.80 (m, 1H), 3.79 (s, 3H), 4,69 (d, 1H, J=15.0 Hz), 4.95 (d, 1H, J=15.0 Hz), 6.37 (s, 1H); $^{13}$C NMR (62.5 MHz) 157.1, 153.9, 132.0, 120.0, 117.1, 105.8, 72.8, 70.5, 64.7, 55.4, 35.8, 29.9, 28.1, 22.5, 21.5, 14.0, 8.8 ppm; IR (neat) 1609, 1465, 1125 cm$^{-1}$; ESI-MS (m/z) 279 (MH$^+$) (FIG. 1).

EXAMPLE 12

To prepare 3,7-dimethyl-6-hexanoxy-8-methoxyischroman (16), isochroman 2 is reacted with 1-bromohexane (cf. The preparation of 12, example 8 above) in approximately 83% yield as a colorless oil: $R_f$ 16=0.85 (hexane:ether, approximately 1:1); $^1$H NMR (250 MHz) δ 0.92 (t, 3H, J=6.4 Hz), 1.35 (d, 3H, J=5.9 Hz), 1.27–1.55 (m, 6H), 1.69–1.83 (m, 2H), 2.11 (s, 3H), 2.65 (d, 2H, J=6.6 Hz), 3.72 (t, 2H, J=6.6 Hz), 3.68–3.81 (m, 1H), 3.79 (s, 3H), 4.69 (d, 1H, J=15.0 Hz), 4.94 (d, 1H, J=15.0 Hz), 6.37 (s, 1H); $^{13}$C NMR (62.5 MHz) 157.0, 153.9, 132.0, 120.0, 117.1, 105.8, 72.8, 70.5, 64.7, 55.4, 35.8, 31.7, 30.2, 25.7, 22.5, 21.5, 13.9, 8.8 ppm; IR (neat) 1609, 1125 cm$^{-1}$; ESI-MS (m/z) 293 (MH$^+$) (FIG. 1).

EXAMPLE 13

To prepare 3,7-dimethyl-6-heptanoxy-8-methoxyisochroman (17), ischroman 2 is reacted with 1-bromoheptane (cf. The preparation of 12, example 8 above) in approximately 81% yield as a colorless oil: $R_f$ 17=0.87 (hexane:ether, approximately 1:1); $^1$H NMR (250 MHz) δ 0.91(t, 3H, J=6.8 Hz), 1.27–1.55 (m, 11H), 1.71–1.82 (m, 2H), 2.11 (s, 3H), 2.65 (d, 2H, J=6.6 Hz), 3.72 (t, 2H, J-8.1 Hz), 3.68–3.80 (m, 1H0, 3.79 (s, 3H) 4.70 (d, 1H, J=15.1 Hz), 4.95 (d, 1H, J=15.1 Hz), 6.38 (s, 1H); $^{13}$C NMR (62.5 MHz) 157.1, 153.9, 132.0, 120.0, 117.1, 105.8, 72.8, 70.5, 64.7, 55.4, 35.8, 31.7, 30.3, 29.1, 22.5, 21.5, 14.0, 8.8 ppm; IR (neat) 1610, 1465, 1125 cm$^{-1}$; ESI-MS (m/z) 307 (MH$^+$) (FIG. 1).

EXAMPLE 14

To prepare 3,7-dimethyl-8-methoxy-6-octanoxyisochroman (18), isochroman 2 is reacted with 1-bromooctane (cf. The preparation of 12, example 8 above) in approximately 89% yield as a colorless oil: $R_f$ 18=0.88 (hexane:ether, approximately 1:1); $^1$H NMR (250 MHz) δ 0.91 (t, 3H, J=6.7 Hz), 1.28–1.53 (m, 13H), 1.71–1.80 (m, 2H), 2.11 (s, 3H), 2.65 (d, 2H, J=6.5 Hz), 3.72 (t, 2H, J=6.6 Hz), 3.68–3.80 (m, 1H), 3.80 (s, 3H0, 4.69 (d, 1H, J=15.1 Hz), 4.95 (d, 1H, J=15.1 Hz), 6.38 (s, 1H); $^{13}$C NMR (62.5 MHz) 157.0, 153.9, 132.0, 120.0, 117.1, 105.8, 72.8, 70.5, 64.7, 55.4, 35.8, 31.7, 30.2, 29.4, 29.2, 26.1, 22.6, 21.5, 14.0, 8.8 ppm; IR (neat) 1610, 1465, 1125 cm$^{-1}$; ESI-MS (m/z) 321 (MH$^+$) (FIG. 1).

EXAMPLE 15

To prepare 3,7-dimethyl-8-methoxy-6-nonanoxyisochroman (19), isochroman 2 is reacted with 1-bromonane (cf. The preparation of 12, example 8 above) in approximately 84% yield as a colorless oil: $R_f$ 19=0.90 (hexane:ether, approximately 1:1) $^1$H NMR (250 MHz) δ 0.90 (t, 3H, J=7.0 Hz), 1.28–1.51 (m, 15H), 1.71–1.82 (m, 2H), 2.11 (s, 3H), 2.65 (d, 2H, J=6.6 Hz), 3.72 (t, 2H, J=6.6 Hz), 3.69–3.81 (m, 1H), 3.79 (s, 3H), 4.69 (d, 1H, J=15.0 Hz), 4.94 (d, 1H, J=15.0 Hz), 6.37 (s, 1H); $^{13}$C NMR (62.5 MHz) 157.1, 153.9, 132.0, 120.0, 117.1, 105.8, 72.8, 70.5, 64.7, 55.4, 35.8, 31.7, 30.2, 29.4, 29.2, 26.0, 22.6, 21.5, 14.0, 8.8 ppm; IR (neat) 1610, 1465, 1125 cm$^{-1}$; ESI-MS (m/z) 335 (MH$^+$) (FIG. 1).

EXAMPLE 16

To prepare 6-acetooxy-3,7-dimethyl-8-methoxyisochroman (20), approximately 84 mg of isochroman 2 is added to a mixture of approximately 92 mg DCC, approximately 5 mg DMAP and approximately 23 μl acetic acid in approximately 2.0 ml CH$_2$Cl$_2$ and stirred at about room temperature for about 2 hours. The solution is filtered and the filtrate is washed with approximately 5% HCl then saturated NaHCO$_3$, dried over anhydrous MgSO$_4$ and concentrated. The residue is chromatographed (elution with hexane:ether, approximately 2:1) to give approximately 85 mg of acetate 20, with a yield of approximately 85%, which is homogeneous by TLC analysis (hexane:ether, approximately 1:1, $R_f$ 20=0.66) as a white crystalline solid: mp approximately 60.5–62° C.; $^1$H NMR (300 MHz) δ 1.33 (s, 3H, J=6.1 Hz), 1.97 (s, 3H), 2.31 (s, 3H), 2.65 (d, 2H, J=6.7 Hz), 3.69–3.80 (m, 1H); $^{13}$C NMR (75.5 MHz) 168.8, 155.9, 145.8, 132.4, 118.9, 116.9, 108.1, 70.5, 63.9, 55.6, 35.6, 21.4, 20.3, 8.8 ppm; IR (neat) 1765, 1622, 1203, 1116 cm$^{-1}$; ESI-MS (m/z) 251 (MH$^+$) (FIG. 1).

EXAMPLE 17

To prepare 3,7-dimethyl-8-methoxy-6-propanoyloxyisochroman (21), isochroman 2 is coupled with propionic acid (cf. Preparation of 20, Example 16 above) in approximately 75% yield as a white crystalline solid: $R_f$ 21=0.67 (hexane:ether, approximately 1:1); mp approximately 68–70° C.; $^1$H NMR (300 MHz) δ 1.29 (t, 3H, J=5.5 Hz), 1.33 (d, 3H, J=6.1 Hz), 1,96 (s, 3H0, 2,59 (q, 2H, J=5.5 Hz), 3.69–3.81 (m, 1H), 3.79 (s, 3H), 4.52 (d, 1H, J=14.8 Hz), 4.68 (d, 1H, J=14.8 Hz), 6.48 (s, 1H); $^{13}$C NMR (75.5 MHz) 171.9, 156.7, 145.7, 132.3, 118.9, 116.9, 107.9, 70.4, 64.0, 55.6, 35.6, 27.3, 21.4, 9.4, 8.8 ppm; IR (neat) 1758, 1261, 1121 cm$^{-1}$; ESI-MS (m/z) 265 (MH$^+$) (FIG. 1).

EXAMPLE 18

To prepare 6-butanoyloxy-3,7-dimethyl-8-methoxyisochroman (22), isochroman 2 is coupled with butanoic acid (cf. Preparation of 20, Example 16 above) in approximately 83% yield as a white crystalline solid: $R_f$ 22=0.72 (hexane:ether, approximately 1:1) mp approximately 56–58° C.; $^1$H NMR (300 MHz) δ 1.31–1.40 (m, 8H), 1.96 (s, 3H), 2.65 (d, 2H, J=6.7 Hz), 2.83 (m 2H), 3.69–3.82 (m, 1H), 3.79 (s, 3H)<4.51 (d, 1H, J=14.6 Hz), 4.69 (d, 1H, J=14.6 Hz), 6.48 (s, 1H); $^{13}$C NMR (75.5 MHz) 174.4, 156.7, 145.6, 132.3, 118.9, 116.9, 107.9, 70.5, 64.0, 55.6, 35.6, 34.1, 21.4, 19.1, 8.7 ppm; IR (neat) 1754, 1261, 1115, 1093 cm$^{-1}$; ESI-MS (m/z) 279 (MH$^+$) (FIG. 1).

EXAMPLE 19

To prepare 3,7-dimethyl-8-methoxy-6-pentanoylisochroman (23), isochroman 2 is coupled with pentanoic acid (cf. Preparation of 20, Example 16 above) in approximately 86% yield as a colorless oil: $R_f$ 23=0.75 (hexane:ether, approximately 1:1); $^1$H NMR (250 MHz) δ 0.98 (t, 3H, J=7.3 Hz), 1.33 (d, 3H, J=6.0 Hz), 1.38=1.50 (m, 2H), 1.70–1.82 (m, 2H), 1.96 (s, 3H), 2.57 (t, 2H, J=7.7 Hz), 2.65 (d, 2H, J=6.7 Hz), 3.69–3.82 (m, 1H), 3.79 (s, 3H), 4.53 (d, 1H, J=14.7 Hz), 4.69 (d, 1H, J=14.7 Hz), 6.48 (s, 1H); $^{13}$C NMR (62.5 MHz) 171.2, 156.6, 145.5, 132.2, 118.9, 116.8, 107.9, 70.4, 64.0, 55.5, 35.5, 33.6, 27.1, 22.3, 21.4, 13.6, 8.8 ppm; IR (neat) 1755, 1261, 1142, 1116, 1093 cm$^{-1}$; ESI-MS (m/z) 293 (MH$^+$) (FIG. 1).

EXAMPLE 20

To prepare 3,7-dimethyl-6-hexanoyloxy-8-methoxyisochroman (24), isochroman 2 is coupled with hexanoic acid (cf. Preparation of 20, Example 16 above) in approximately 75% yield as a colorless oil: $R_f$ 24=0.77 (Hexane:ether, approximately 1:1); $^1$H NMR (250 MHz) δ 0.94 (t, 3H, J=6.7 Hz), 1.33 (d, 3H, J=6.0 Hz), 1.35–1.46 (m, 4H), 1.71–1.97 (m, 2H), 2.06 (s, 3H), 2.56 (t, 2H, J=7.7 Hz), 2.65 (d, 2H, J=6.7 Hz), 3.70–3.81 (m, 1H), 3.79 (s, 3H), 4.52 (d, 1H, J=14.7 Hz), 4.69 (d, 1H, J=14.7 Hz), 6.49 (s, 1H); $^{13}$C NMR (62.5 MHz) 171.2, 156.6, 145.5, 132.2, 118.9, 116.8, 107.9, 70.4, 64.0, 55.5, 35.5, 33.8, 31.2, 24.7, 22.2, 21.4, 13.8, 8.8 ppm; IR (neat) 1757, 1261, 1142, 1116, 1093 cm$^{-1}$; ESI-MS (m/z) 307 (MH$^+$) (FIG. 1).

EXAMPLE 21

To prepare 3,7-dimethyl-6-heptanoyloxy-8-methoxyisochroman (25), isochroman 2 is coupled with heptanoic acid (cf. Preparation of 20, Example 16 above) in approximately 88% yield as a colorless oil: $R_f$ 25=0.79 (hexane:ether, approximately 1:1); $^1$H NMR (250 MHz) δ 0.89 (t,3H, J=5.8 Hz), 1.26–1.41 (m, 9H), 1.71–1.82 (m, 2H), 1.96 (s, 3H), 2.56 (t, 2H, J=7.6 Hz), 2.65 (d, 2H, J=6.7 Hz), 3.71–3.81 (m, 1H), 3.79 (s, 3H), 4.52 (d, 1H, J=14.7 Hz), 4.69 (d, 1H, J=14.7 Hz), 6.48 (s, 1H); $^{13}$C NMR (62.5 MHz) 171.2, 156.6, 145.5, 132.2, 118.9, 116.8, 107.9, 70.4, 64.0, 55.5, 35.5, 33.9, 31.3, 28.8, 24.9, 22.4, 21.4, 13.9, 8.8, 5.1 ppm; IR (neat) 1757, 1261, 1141, 1115, 1094 cm$^{-1}$; ESI-MS (m/z) 321 (MH$^+$) (FIG. 1).

EXAMPLE 22

To prepare 3,7-dimethyl-8-methoxy-6-octanoyloxyisochroman (26), isochroman 2 is coupled with octanoic acid (cf. Preparation of 20, Example 16 above) in approximately 72% yield as a colorless oil: $R_f$ 26=0.83 (hexane:ether, approximately 1:1); $^1$H NMR (250 MHz) δ 0.91 (t, 3H, J=6.9 Hz), 1.30–1.46 (m, 1H), 1.71–1.83 (m, 2H), 2.56 (t, 2H, J=7.8 Hz), 2.66 (d, 2H, J=6.7 Hz), 3.71–3.82 (m, 1H), 3.79 (s, 3H), 4.53 (d, 1H, J=14.7 Hz), 4.69 (d, 1H, J=14.7 Hz), 6.48 (s, 1H); $^{13}$C NMR (62.5 MHz) 171.2, 156.6, 145.5, 132.2, 118.9, 116.8, 107.9, 70.4, 64.0, 55.5, 35.6, 33.9, 31.5, 29.1, 28.8, 25.0, 22.5, 21.4, 13.9, 12.3, 8.8 ppm; IR (neat) 1757, 1261, 1141, 1116, 1094, cm$^{-1}$; ESI-MS (m/z) 335 (MH$^+$) (FIG. 1).

EXAMPLE 23

To prepare 3,7-dimethyl-8-methoxy-6-nonanoyloxyisochroman (27), isochroman 2 is coupled with nonanoic acid (cf. Preparation of 20, Example 16 above) in approximately 70% yield as a colorless oil: R$_f$ 27=0.85 (hexane:ether, approximately 1:1); $^1$H NMR (250 MHz) δ 0.90 (t, 3H, J=7.0 Hz), 1.29–1.44 (m, 3H), 1.71–1.81 (m, 2H), 2.56 (t, 2H, J=7.6 Hz), 2.66 (d, 2H, J=6.7 Hz), 3.70–3.81 (m, 1H), 3.79 (s, 3H), 4.52 (d, 1H, J=14.7 Hz), 4.69 (d, 1H, J=14.7 Hz), 6.49 (s, 1H); $^{13}$C NMR (62.5 MHz) 171.2, 156.6, 145.5, 132.2, 118.9, 116.8, 107.9, 70.4, 64.0, 55.5, 35.5, 33.9, 31.7, 29.1, 29.0, 25.0, 22.5, 21.4, 13.9, 8.8 ppm; IR (neat) 1757, 1260, 1141, 1117, 1094 cm$^{-1}$; ESI-MS (m/z) 349 (MH$^+$) (FIG. 1).

EXAMPLE 24

To prepare 3,7-dimethyl-8 methoxy-6-phenylthiomethoxyisochroman (30), approximately 1.14 grams isochroman 2 is added to a stirred suspension containing approximately 0.33 grams of an approximately 60% dispersion in mineral oil of NaH in approximately 20 ml HMPA at about 0° C. After about 30 minutes, approximately 1.5 ml of chloromethyl phenyl sulfide and approximately 1.0 grams of NaI is added and the mixture is stirred at about room temperature for about 2 hours. Approximately 25 ml of ether and approximately 15 ml of water are then added and the aqueous layer is saturated with NaCl and extracted about 3 times with about 15 ml of ether. The combined organic layers are dried over anhydrous MgSO$_4$, concentrated and the resulting residue is chromatographed (elution with hexane:ether, approximately 2:1) to give approximately 1.36 grams of ether 30, in a yield of approximately 76%, as a pale yellow solid: R$_f$ 30=0.75 (hexane:ether, approximately 1:1); mp approximately 102.5–104° C.; $^1$H NMR (250 MHz) δ 1.32 (d, 3H, J=6.0 Hz), 2.09 (s, 3H), 2.64 (d, 2H, J-6.9), 3.67–3.81 (m, 1H), 3.79 (s, 3H), 4.67 (d, 1H, J=15.2 Hz), 4.93 (d, 1H, J=15.2 Hz), 5.29 (s, 2H), 6.41 (s, 1H), 7.22–7.36 (m, 3H), 7.50–7.54 (m, 2H); $^{13}$C NMR (62.5 MHz) 157.2, 152.7, 135.7, 132.4, 129.9, 129.0, 126.9, 120.4, 117.0, 106.8, 77.6, 70.5, 65.2, 55.6, 35.8, 21.6, 9.7 ppm; IR (neat) 1612, 1582, 1116 cm$^{-1}$; ESI-MS (m/z) 331 (MH$^+$) (FIG. 2).

EXAMPLE 25

To prepare 3,7-dimethyl-8-hydroxy-6-phenylthiomethoxyisochroman (31), approximately 7.0 ml of ethanethiol is added to a stirred suspension of approximately 5.7 grams of an approximately 60% dispersion in mineral oil of NaH in approximately 100 ml DMF at about 0° C. After about 1 hour, approximately 1.56 grams of isochroman 30 is added and the mixture is heated to approximately 120° C. for approximately 8 hours. The reaction is quenched with saturated NH$_4$Cl, acidified with approximately 10% HCl, saturated with NaCl and extracted about 5 times with approximately 40 ml ether. The combined organic extracts are stirred vigorously with approximately 50 grams CuSO$_4$ for about 1 hour and the solids are suction filtered. The filtrate is concentrated and the residue chromatographed (elution with hexanes:ether, approximately 2:1) to give approximately 1.19 grams of isochroman 31, in an approximately 80% yield, as a white crystalline solid: R$_f$ 31=0.55 (hexane:ether, approximately 1:1); mp approximately 107.5–109° C.; $^1$H NMR (250 MHz) δ 1.31(d, 3H, J=5.1 Hz), 2.10 (s, 3H), 2.53 (d, 2H, J=5.1 Hz), 3.65–3.76 (m, 1H), 4.65 (d, 1H, J=12.5 Hz), 4.93 (d, 1H, J=12.5 Hz), 5.27 (s, 1H), 6.31 (s, 1H), 7.21–7.33 (m, 3H), 7.49 (d, 2H, J+6.1 Hz); $^{13}$C NMR (62.5 MHz) 153.6, 152.9, 135.5, 132.5, 129.9, 127.0, 120.1, 115.2, 111.2, 77.6, 70.8, 65.1, 35.3, 21.4, 9.6 ppm; IR (neat) 3500–3150, 1614, 1066 cm$^{-1}$; ESI-MS (m/z) 317 (MH$^+$) (FIG. 2).

EXAMPLE 26

To prepare 3,7-dimethyl-8-hydroxy-6-methoxyisochroman (3), approximately 0.83 gram of 31 in approximately 20 ml ethanol is added to approximately 1.0 grams of W-6 Raney Nickel and the mixture is refluxed for approximately 3 hours. The mixture is filtered on a bed of celite and concentrated to give approximately 0.50 grams of phenol 3, in a yield of approximately 92%, which is homogeneous by TLC analysis (hexane:ether, approximately 1:1. R$_f$ 3=0.51) as a white crystalline solid: mp approximately 143–145° C.; $^1$H NMR (250 MHz) δ 1.33 (d, 3H, J=6.0 Hz), 2.14 (s, 3H), 2.59 (d, 2H, J=6.6 Hz), 3.68 (s, 3H), 3.67–3.80 (m, 1H), 4.68 (d, 1H, J=15.1 Hz), 4.93 (d, 1H, J=15.1 Hz), 4.94 (s, 1H), 6.35 (s, 1H); $^{13}$C NMR (62.5 MHz) 154.9, 153.3, 132.5, 119.8, 114.9, 110.4, 70.6, 64.5, 60.1, 35.3, 21.4, 8.4 ppm; IR (neat) 3500–3150, 1614, 1098 cm$^{-1}$; ESI-MS (m/z) 209 (MH$^+$) (FIG. 2).

EXAMPLE 27

To prepare 3,7-dimethyl-8-ethoxy-6-methoxyisochroman (33), isochroman 3 is reacted with iodoethane (cf. The preparation of 12, Example 8) in approximately 81% yield as a colorless oil: R$_f$ 33=0.80 (hexane:ether, approximately 1:1); $^1$H NMR (300 MHz) δ 1.34 (d, 3H, J=6.1 Hz), 1.42 (t, 3H, J=7.0 Hz), 2.12 (s, 3H), 2.63 (d, 2H, J=6.2 Hz), 3.69 (s, 3H), 3.70–3.82 (m, 1H), 3.98 (q, 2H, J=7.0 Hz), 4.69 (d, 1H, J=15.2 Hz), 4.93 (d, 1H, J=15.2 Hz), 6.37 (s, 1H); $^{13}$C NMR (75.5 MHz) 156.5, 154.8, 132.1, 119.8, 117.3, 107.2, 70.6, 64.5, 63.8, 60.0, 35.8, 21.5, 14.9, 8.6 ppm; IR (neat) 1608, 1261, 1121 cm$^{-1}$; ESI-MS (m/z) 237 (MH$^+$) (FIG. 2).

EXAMPLE 28

To prepare 3,7-dimethyl-6-methoxy-8-propoxyisochroman (34), isochroman 3 is reacted with 1-bromopropane (cf. The preparation of 12, Example 8) in approximately 63% yield as a colorless oil: R$_f$ 34=0.81 (hexane:ether, approximately 1:1); $^1$H NMR (300 MHz) δ 106 (t, 3H, J=7.4 Hz), 1.34 (d, 3H, J=6.1 Hz), 1.76–1.87 (m, 2H), 2.13 (s, 3H), 2.63 (d, 2H, J=6.3 Hz), 3.70–3.80 (m, 1H), 3.89 (t, 2H, J=6.3 Hz), 4.69 (d, 1H, J=15.0 Hz), 4.93 (d, 1H, J=15.0 Hz), 6.37 (s, 1H); $^{13}$C NMR (75.5 MHz) 156.7, 154.8, 132.1, 119.7, 117.3, 107.1, 70.6, 69.7, 64.6, 50.1, 35.8, 22.6, 21.5, 10.6, 8.6 ppm; IR (neat) 1610, 1262, 1120 cm$^{-1}$; ESI-MS (m/z) 251 (MH$^+$) (FIG. 2).

EXAMPLE 29

To prepare 8-butoxy-3,7-dimethyl-6-methoxyisochroman (35), isochroman 3 is reacted with 1-bromobutane (cf. The preparation of 12, Example 8) in approximately 66% yield as a colorless oil: R$_f$ 35=0.83 (hexane:ether, approximately 1:1); $^1$H NMR (300 MHz) δ 0.98 (t, 3H, J=7.6 Hz), 1.34 (d, 3H, J=6.1 Hz), 1.45–1.57 (m, 2H), 1.73–1.82 (m, 2H), 2.12 (s, 3H), 2.63 (d, 2H, J=6.4 Hz), 3.60 (s, 3H), 3.69–3.80 (m, 1H), 3.92 (t, 2H, J=6.4 Hz), 4.69 (d, 1H, J=15.0 Hz), 4.93 (d, 1H, J=15.0 Hz), 6.37(s, 1H); $^{13}$C NMR (75.5 MHz) 156.7, 154.9, 132.1, 119.8, 117.7, 107.1, 70.6, 67.9, 64.6, 60.1, 35.8, 31.4, 21.5, 19.3, 13.8, 8.6 ppm; IR (neat) 1609, 1262, 1119 cm$^{-1}$; ESI-MS (m/z) 265 (MH$^+$) (FIG. 2).

EXAMPLE 30

To prepare 3,7-dimethyl-6-methoxy-8-pentanoxyisochroman (36), isochroman 3 is reacted with 1-bromopentane (cf. The preparation of 12, Example 8) in approximately 75% yield as a colorless oil: R$_f$ 36=0.83 (hexane:ether, approximately 1:1); $^1$H NMR (300 MHz) δ 0.94 (t, 3H, J=7.0 Hz), 1.34 (d, 3H, J=6.1 Hz), 1.35–1.50 (m, 4H), 1.74–1.84 (m, 2H), 2.12 (s, 3H), 2.63 (d, 2H, J=6.4 Hz), 3.69 (s, 3H), 3.70–3.79 (m, 1H), 3.91 (t, 2H, J=6.3 Hz), 4.69 (d, 1H, J=15.0 Hz), 4.93 (d, 1H, J=15.0 Hz), 6.37 (s, 1H); $^{13}$C NMR (75.5 MHz) 162.9, 156.7, 154.8, 132.1, 119.7, 117.3, 107.1, 70.6, 68.2, 64.6, 60.0, 35.8, 29.0, 28.3, 22.4, 21.5, 14.0, 8.6 ppm; IR (neat) 1609, 1262, 1091 cm$^{-1}$; ESI-MS (m/z) 279 (MH$^+$) (FIG. 2).

EXAMPLE 31

To prepare 3,7-dimethyl-8-hexanoxy-6-methoxyisochroman (37), isochroman 3 is reacted with 1-bromohexane (cf. The preparation of 12, Example 8) in approximately 71% yield as a colorless oil: R$_f$ 37=0.85 (hexane:ether, approximately 1:1); $^1$H NMR (300 MHz) δ 0.92 (t, 3H, J=6.9 Hz), 1.34 (d, 3H, J=6.1 Hz), 1.31–1.54 (m, 6H), 1.73–1.82 (m, 2H), 2.12 (s, 3H), 2.63 (d, 2H, J=6.3 Nz), 3.69 (s, 3H), 3.70–3.79 (m, 1H), 3.92 (t, 2H, J=6.6 Hz), 4.69 (d, 1H, J=15.0 Hz), 4.93 (d, 1H, J=15.0 Hz), 6.37 (s, 1H); $^{13}$C NMR (75.5 MHz) 156.7, 154.8, 132.1, 119.7, 117.3, 107.1, 70.6, 68.2, 64.6, 60.0, 35.8, 31.5, 29.3, 25.8, 22.6, 21.5, 13.9, 8.6 ppm; IR (neat) 1609, 1262, 1118, 1091 cm$^{-1}$; ESI-MS (m/z) 293 (MH$^+$) (FIG. 2).

EXAMPLE 32

To prepare 3,7-dimethyl-8-heptanoxy-6-methoxyisochroman (38), isochroman 3 is reacted with 1-bromoheptane (cf. The preparation of 12, Example 8) in approximately 70% yield as a colorless oil: R$_f$ 38=0.86 (hexane:ether, approximately 1:1); $^1$H NMR (300 MHz) δ 0.90 (t, 3H, J=6.9 Hz), 1.34 (d, 3H, J=6.1 Hz), 1.29–1.51 (m, 8H), 1.72–1.83 (m, 2H), 2.12 (s, 3H), 2.63 (d, 2H, J=6.4 Hz), 3.69 (s, 3H), 3.69–3.79 (m, 1H), 3.91 (t, 2H, J=6.3 Hz), 4.69 (d, 1H, J=6.4 Hz), 3.69 (s, 3H), 3.69–3.79 (m, 1H), 3.91 (t, 2H, J=6.3 Hz), 4.69 (d, 1H, J=15.0 Hz), 4.93 (d, 1H, J=15.0 Hz), 6.37 (s, 1H); $^{13}$C NMR (75.5 MHz) 156.7, 154.8, 132.1, 119.7, 117.3, 107.1, 70.6, 68.2, 64.6, 60.1, 35.8, 31.8, 29.3, 29.0, 26.1, 22.6, 21.5, 14.0, 8.6 ppm; IR (neat) 1609, 1262, 1118, 1092 cm$^{-1}$; ESI-MS (m/z) 307 (MH$^+$) (FIG. 2 ).

EXAMPLE 33

To prepare 3,7-dimethyl-6-methoxy-8-octanoxyisochroman (39), isochroman 3 is reacted with 1-bromooctane (cf. The preparation of 12, Example 8) in approximately 72% yield as a colorless oil: R$_f$ 39=0.89 (hexane:ether, approximately 1:1); $^1$H NMR (300 MHz) δ 0.89 (t, 3H, J=6.7 Hz), 1.29–1.51 (m, 13H), 1.74–1.83 (m, 2H), 2.12 (s, 3H), 2.63 (d, 2H, (J=6.4 Hz), 3.69 (s, 3H), 3.68–3.79 (m, 1H), 3.91 (t, 2H, J=6.4 Hz), 4.69 (d, 1H, J=15.0 Hz), 4.93 (d, 1H, J=15.0 Hz), 6.37 (s, 1H); $^{13}$C NMR (75.5 MHz) 156.8, 155.2, 132.1, 119.7, 117.6, 107.1, 70.6, 68.2, 64.6, 60.1, 35.8, 31.8, 29.3, 29.2, 26.1, 22.6, 21.6, 14.1, 8.6 ppm; IR (neat) 1610, 1262, 1118, 1092 cm$^{-1}$; ESI-MS (m/z) 321 (MH$^+$) (FIG. 2).

EXAMPLE 34

To prepare 3,7-dimethyl-6-methoxy-8-nonanoxyisochroman (40), isochroman 3 is reacted with 1-bromononane (cf. The preparation of 12, Example 8) in approximately 62% yield as a colorless oil: R$_f$ 40=0.91 (hexane:ether, approximately 1:1); $^1$H NMR (250 MHz) δ 0.89 (t, 3H, J=6.3 Hz), 1.28–1.51 (m, 15H), 1.73–1.83 (m, 2H), 2.12 (s, 3H), 2.63 (d, 2H, J=6.6 Hz), 3.69 (s, 3H), 3.69–3.80 (m, 1H), 3.91 (t, 2H, J=6.2 Hz), 4.70 (d, 1H, J=15.0 Hz), 4.94 (d, 1H, J=15.0 Hz), 6.37 (s, 1H); $^{13}$C NMR (62.5 MHz) 156.7, 154.7, 132.0, 119.6, 117.2, 107.0, 70.5, 68.2, 64.5, 60.0, 35.8, 31.8, 29.4, 29.3, 26.0, 22.6, 21.5, 14.0, 8.6 ppm; IR (neat) 1609, 1262, 1118, 1091 cm$^{-1}$; ESI-MS (m/z) 321 (MH$^+$) (FIG. 2).

EXAMPLE 35

To prepare 8-acetoxy-3,7-dimethyl-6-methoxyisochroman (42), isochroman 3 is coupled with acetic acid (cf. Preparation of 20, Example 16 above) in approximately 72% yield as a white crystalline solid: R$_f$ 2=0.61 (hexane:ether, approximately 1:1); mp approximately 83–84° C.; $^1$H NMR (250 MHz) δ 1.33 (d, 3H, J=6.1 Hz), 2.06 (s, 3H), 2.31 (s, 3H), 2.64 (d 2H, J=6.8 Hz), 3.70 (s, 3H), 3.68–3.80 (m, 1H), 4.70 (d, 1H, J=15.6 Hz), 4.97 (d, 1H, J=15.6 Hz), 6.59 (s, 1H); $^{13}$C NMR (62.5 MHz) 169.2, 154.8, 148.4, 132.9, 125.7, 121.0, 117.5, 70.4, 64.5, 60.1, 35.2, 21.4, 20.7, 14.6, 9.1 ppm; IR (neat) 1761, 1206, 1119, 1085 cm$^{-1}$; ESI-MS (m/z) 251 (MH$^+$) (FIG. 2).

EXAMPLE 36

To prepare 3,7-dimethyl-6-methoxy-8-propanoxyisochroman (43), isochroman 3 is coupled with propionic acid (cf. Preparation of 20, Example 16 above) in approximately 74% yield as a white crystalline solid: R$_f$ 43=0.64 (hexane:ether, approximately 1:1); mp approximately 58–59° C.; $^1$H NMR (300 MHz) δ 1.25–1.34 (m, 6H), 2.05 (s, 3H), 2.55–2.65 (m, 4H), 3.70 (s, 3H), 3.64–3.78 (m, 1H), 4.70 (d, 1H, J=15.2 Hz), 4.97 (d, 1H, J=15.2 Hz), 6.58 (s, 1H); $^{13}$C NMR (75.5 MHz) 172.8, 154.9, 148.5, 132.9, 125.6, 121.1, 117.5, 70.4, 64.6, 60.1, 35.3, 27.5, 21.5, 9.2 ppm; IR (neat) 1758, 1357, 1142, 1088 cm$^{-1}$; ESI-MS (m/z) 265 (MH$^+$) (FIG. 2).

EXAMPLE 37

To prepare 8-butanoyloxy-3,7-dimethyl-6-methoxyisochroman (44), isochroman 3 is coupled with butanoic acid (cf. Preparation of 20, Example 16 above) in approximately 77% yield as a white crystalline solid: R$_f$ 44=0.65 (hexane:ether, approximately 1:1); mp approximately 59–60° C.; $^1$H NMR (250 MHz) δ 1.25–1.40 (m, 8H), 2.05 (s, 3H), 2.64 (d, 2H, J=6.8 Hz), 2.77–2.88 (m, 2H), 3.69 (s, 3H), 3.70–3.79 (m, 1H), 4.70 (d, 1H, J=15.5 Hz), 4.97 (d, 1H, J=15.5 Hz), 6.56 (s, 1H); $^{13}$C NMR (62.5 MHz) 175.3, 154.7, 148.4, 132.8, 125.4, 121.1, 117.4, 70.4, 64.4, 60.1, 35.2, 34.0, 21.4, 18.9, 9.1 ppm; IR (neat) 1754, 1358, 1120, 1084 cm$^{-1}$; ESI-MS (m/z) 279 (MH$^+$) (FIG. 2).

EXAMPLE 38

To prepare 3,7-dimethyl-6-methoxy-8-pentanoylisochroman (45), isochroman 3 is coupled with pentanoic acid (cf. Preparation of 20, Example 16 above) in approximately 83% yield as a colorless oil: R$_f$ 45=0.70 (hexane:ether, approximately 1:1); $^1$H NMR (300 MHz) δ 0.97 (t, 3H, J=7.1 Hz), 1.33 (d, 3H, J=6.1 Hz), 1.41–1.49 (m, 2H), 1.71–1.80 (m, 2H), 2.05 (s, 3H), 2.57 (t, 2H, J+7.4 Hz), 2.64 (d, 2H, J=6.7 Hz), 3.70 (s, 3H), 3.67–3.80 (m, 1H), 4.70 (d, 1H, J=15.6 Hz), 4.97 (d, 1H, J=15.6 Hz), 6.57 (s, 1H); $^{13}$C NMR (75.5 MHz) 172.3, 154.8, 148.7, 132.8, 125.7, 121.1, 117.5, 70.4, 64.6, 60.1, 35.3, 33.9, 27.1, 22.3, 21.5, 13.7, 9.2 ppm; IR (neat) 1756, 1358, 1142, 1086 cm$^{-1}$; ESI-MS (m/z) 293 (MH$^+$) (FIG. 2).

EXAMPLE 39

To prepare 3,7-dimethyl-8-hexanoyloxy-6-methoxyisochroman (46), isochroman 3 is coupled to hexanoic acid (cf. Preparation of 20, Example 16 above) in approximately 79% yield as a colorless oil: R$_f$ 46=0.73 (hexane:ether, approximately 1:1) $^1$H NMR (250 MHz) δ 0.94 (t, 3H, J=7.4 Hz), 1.33 (d, 3H, J=6.3 Hz), 1.34–1.43 (m, 4H), 1.71–1.81 (m, 2H), 2.05 (s, 3H), 2.56 (t, 2H, J=7.4 Hz), 2.64 (d, 2H, J=6.8 Hz), 3.70 (s, 3H), 3.69–3.81 (m, 1H), 4.70 (d, 1H, J=15.7 Hz), 4.97 (d, 1H, J=15.7 Hz), 6.58 (s, 1H); $^{13}$C NMR (62.5 MHz) 172.0, 154.8, 148.4, 132.8, 125.5, 121.0, 117.5, 70.4, 64.5, 60.1, 35.2, 34.1, 31.2, 24.6, 22.2, 21.4, 13.8, 9.2 ppm; IR (neat) 1757, 1357,1142, 1086 cm$^{-1}$; ESI-MS (m/z) 307 (MH$^+$) (FIG. 2).

EXAMPLE 40

To prepare 3,7-dimethyl-8-heptanoyloxy-6-methoxyisochroman (47), isochroman 3 is coupled with heptanoic acid (cf. Preparation of 20, Example 16 above) in approximately 74% yield as a colorless oil: R$_f$ 47 =0.78 (hexane:ether, approximately 1:1); $^1$H NMR (300 MHz) δ 0.89 (t, 3H, J=6.0 Hz), 1.29–1.52 (m, 9H), 1.70–1.81 (m, 2H), 2.05 (s, 3H), 2.56 (t, 2H, J=7.6 Hz), 2.64 (d, 2H, J=6.8 Hz), 3.69 (s, 3H), 3.68–3.80 (m, 1H), 4.70 (d, 1H, J=15.6 Hz), 4.97 (d, 1H, J=15.6 Hz), 6.57 (s, 1H); $^{13}$C NMR (75.5 MHz) 172.1, 154.8, 148.5, 132.9, 125.6, 121.1, 117.6, 70.4, 64.6, 60.1, 35.3, 34.2, 31.7, 29.1, 25.0, 22.6, 21.5, 14.1, 9.2 ppm; IR (neat) 1757, 1357, 1140, 1086 cm$^{-1}$; ESI-MS (m/z) 321 (MH$^+$) (FIG. 2).

EXAMPLE 41

To prepare 3,7-dimethyl-6-methoxy-8-octanoylisochroman (48), isochroman 3 is coupled with octanoic acid (cf. Preparation of 20, Example 16 above) in approximately 80% yield as a colorless oil: R$_f$ 48 =0.79 (hexane:ether, approximately 1:1); $^1$H NMR (300 MHz) δ 0.90 (t, 3H, J=6.8 Mhz), 1.31–1.51 (m, 11H), 1.71–1.81 (m, 2H), 2.05 (s, 3H), 2.56 (t, 2H, J=7.5 Hz), 2.64 (d, 2H, J=6.8 Hz), 3.69 (s, 3H), 3.68–3.80 (m, 1H), 4.70 (d, 1H, J=15.5 Hz), 4.97 (d, 1H, J+15.5 Hz), 6.57 (s, 1H); $^{13}$C NMR (75.5 MHz) 172.1, 154.9, 148.3, 133.2, 125.8, 121.1, 117.5, 70.4, 64.6, 60.1, 35.3, 34.2, 31.6, 29.1, 28.9, 25.0, 22.5, 21.5, 14.0, 9.2 ppm; IR (neat) 1757, 1358, 1141, 1086 cm$^{-1}$; ESI-MS (m/z) 335 (MH$^+$) (FIG. 2).

EXAMPLE 42

To prepare 3,7-dimethyl-6-methoxy-8-nonanoyloxyisochroman (49), isochroman 3 is coupled with nonanoic acid (cf. Preparation of 20, Example 16 above) in approximately 78% yield as a colorless oil: R$_f$ 49=0.84 (hexane:ether, approximately 1:1); $^1$H NMR (300 MHz) δ 0.90 (t, 3H, J=6.8 Hz), 1.28–1.49 (m, 13H), 1.71–1.81 (m, 2H), 2.05 (s, 3H), 2.57 (t, 2H, J=7.6 Hz), 2.65 (s, 2H, J=6.7 Hz), 3.69 (s, 3H), 3.68–3.79 (m, 1H), 4.70 (d, 1H, J=15.5 Hz), 4.97 (d, 1H, J=15.5 Hz), 6.57 (s, 1H); $^{13}$C NMR (75.5 MHz) 172.1, 154.9, 148.4, 132.9, 125.6, 121.1, 117.5, 70.4, 64.6, 60.1, 35.3, 34.1, 31.4, 28.8, 24.9, 22.4, 21.5, 13.9, 9.2 ppm; IR (neat) 1757, 1358, 1141, 1095 cm$^{-1}$; ESI-MS (m/z) 349 (MH$^+$) (FIG. 2).

EXAMPLE 43

Bioassays of the derivatives of isochroman 2 and 3 were conducted by the etiolated wheat coleptile bioassay of Hancock et al (J. Exp. Biol., Volume 15, 166–176, 1964; herein incorporated by reference). The bioassay is prepared by sowing wheat seed (*Triticum aestivium* L cv. Wakeland) on moist vermiculite in plastic trays which are sealed with aluminum foil and kept in the dark at 22°±1.0° C. for about four days. Ten approximately 4 mm sections are cut from each seedling and placed in test tubes containing 2 ml of phosphate-citrate buffer at pH 5.6 supplemented with approximately 2% sucrose (Nitsch et al, Plant Physiol., Volume 31, 94–111, 1956; herein incorporated by reference) and one of 10$^{-3}$, 10$^{-4}$, 10$^{-5}$ and 10$^{-6}$M of each derivatives 12–27 and 33–49 for 18 hours (Cutler, Proc. 11th Ann. Meeting Plant Growth Reg. Soc. America, 1–9, 1984; herein incorporated by reference). Following this incubation, the coleoptile sections are removed, measured and recorded. The data were statistically analyzed (Kurtz et al, Technometrics, Volume 7, 95–161, 1965). The results of duplicate experiments are shown below in Tables 1 and 2.

The foregoing detailed description is for the purpose of illustration. Such detail is solely for that purpose and those skilled in the art can make variations therein without departing from the spirit and scope of the invention.

TABLE 1

Wheat Coleoptile Assay Using Derivatives of 3,7-dimethyl-8-hydroxy-6-methoxyisochroman.

Wheat Coleoptile Assay (mm × 3)

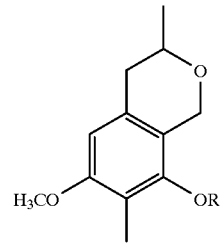

| R | 10$^{-3}$ | 10$^{-4}$ | 10$^{-5}$ | 10$^{-6}$ M |
|---|---|---|---|---|
| Ethyl | 12.0* | 13.7* | 17.0 | 17.2 |
| Propyl | 12.0* | 13.5* | 17.1 | 17.0 |
| Butyl | 12.0* | 13.5* | 17.0 | 17.0 |
| Hexyl | 15.2* | 17.0 | 17.0 | 17.1 |
| Heptyl | 15.0* | 17.0 | 17.0 | 17.1 |
| Octyl | 17.1 | 17.0 | 17.7 | 17.1 |
| Nonyl | 14.7* | 17.0 | 17.1 | 17.1 |

R

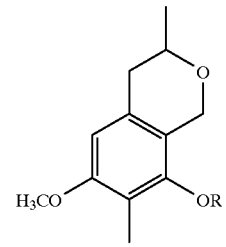

| | | | | |
|---|---|---|---|---|
| Acetate | 12.0* | 15.1* | 17.0 | 17.1 |
| Propanate | 12.0* | 14.3* | 17.1 | 17.0 |
| Butanoate | 12.0* | 14.8* | 17.1 | 17.1 |
| Pentanoate | 12.0* | 13.2* | 17.0 | 17.1 |
| Hexanoate | 13.0* | 14.3* | 17.0 | 17.0 |

TABLE 1-continued

Wheat Coleoptile Assay Using Derivatives of 3,7-dimethyl-8-hydroxy-6-methoxyisochroman.

| | | | | |
|---|---|---|---|---|
| Heptanoate | 17.0 | 17.0 | 17.1 | 17.0 |
| Octanoate | 17.1 | 17.1 | 17.1 | 17.1 |
| Nonanoate | 17.0 | 17.1 | 17.1 | 17.1 |

Controls: 17.1 mm(×3)
*Significant Inhibition (P < 0.01)
Initial Length of Coleoptiles: 12.0 mm(×3)

TABLE 2

Wheat Coleoptile Assay Using Derivatives of 3,7-dimethyl-6-hydroxy-8-methoxyisochroman.

Wheat Coleoptile Assay (mm × 3)

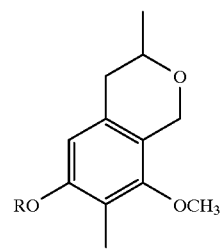

| R | $10^{-3}$ | $10^{-4}$ | $10^{-5}$ | $10^{-6}$ M |
|---|---|---|---|---|
| Ethyl | 13.0* | 14.5* | 17.0 | 17.1 |
| Propyl | 13.1* | 14.4* | 17.2 | 17.2 |
| Butyl | 12.0* | 14.1* | 17.0 | 17.1 |
| Pentyl | 12.0* | 13.1* | 17.1 | 17.1 |
| Hexyl | 15.1* | 15.1* | 17.1 | 17.0 |
| Heptyl | 15.0* | 17.0 | 17.1 | 17.1 |
| Octyl | 15.9* | 17.0 | 17.1 | 17.1 |
| Nonyl | 17.1 | 17.1 | 17.1 | 17.1 |
| R | 12.0* | 17.0 | 17.1 | 17.1 |
| Acetate | 12.0* | 17.0 | 17.1 | 17.1 |
| Propanate | 12.0* | 15.1* | 17.0 | 17.1 |
| Butanoate | 12.0* | 14.0* | 17.1 | 17.1 |
| Pentanoate | 12.1* | 14.0* | 17.1 | 17.1 |
| Hexanoate | 13.2* | 14.5* | 17.1 | 17.0 |
| Heptanoate | 13.0* | 15.8* | 17.1 | 17.1 |
| Octanoate | 13.1* | 13.9* | 17.0 | 17.1 |
| Nonanoate | 17.0 | 17.0 | 17.1 | 17.1 |

Controls: 17.1 mm(×3)
*Significant Inhibition (P < 0.01)
Initial Length of Coleoptiles: 12.0 mm(×3)

We claim:

1. A method for synthesizing isochromans comprising reacting 3,7-dimethyl-6,8-dimethoxyisochroman with sodium ethyl thiolate or hydride reagents in DMF to produce 3,7-dimethyl-6-hydroxy-8-methoxyisochroman.

2. The method of claim 1 wherein the reaction takes place under refluxing conditions.

3. The method of claim 1 further comprising reacting 3,7-dimethyl-6-hydroxy-8-methoxyisochroman with sodium hydride and a halogenated alkane to produce an ether derivative.

4. The method of claim 1 further comprising reacting 3,7-dimethyl-6-hydroxy-8-methoxyisochroman with DCC and an aliphatic acid to produce an ester derivative.

5. The method of claim 1 further comprising
reacting 3,7-dimethyl-6-hydroxy-8-methoxyisochroman with sodium hydride and phenylthiomethyl chloride to produce a phenylmethyl ether,
treating the phenylmethyl ether with sodium ethyl thiolate or hydride reagents in order to selectively remove the C(8) methyl ether to produce 3,7-dimethyl-8-hydroxy-6-phenylthiomethoxyisochroman,
desulfurizing 3,7-dimethyl-8-hydroxy-6-phenylthiomethoxyisochroman to produce 3,7-dimethyl-8-hydroxy-6-methoxyisochroman.

6. The method of claim 5 further comprising reacting 3,7-dimethyl-8-hydroxy-6-methoxyisochroman with sodium hydride and a halogenated alkane to produce an ether derivative.

7. The method of claim 5 further comprising reacting 3,7-dimethyl-8-hydroxy-6-methoxyisochroman with DCC and an aliphatic acid to produce an ester derivative.

8. A method for synthesizing isochromans comprising
methylating 3,5-dihydroxy-4-methylbenzoic acid to provide a dimethyl ether,
converting the hydroxyl groups to leaving group of said ether,
reacting said converted ether compound with a vinyl magnesium bromide or a vinyllithium to produce an olefin,
hydroxylating said olefin to produce a secondary alcohol,
treating said secondary alcohol with sodium hydride and chloromethyl ether to produce 3,7-dimethyl-6,8-dimethoxyisochroman.

9. A compound selected from the group consisting of 3,7-dimethyl-6-ethoxy-8-methoxyisochroman, 3,7-dimethyl-8-methoxy-6-propoxyisochroman, 6-butoxy-3,7-dimethyl-8-methoxyisochroman, 3,7-dimethyl-8-methoxy-6-pentanoxyisochroman and 3,7-dimethyl-6-hexanoxy-8-methoxyisochroman.

10. A compound selected from the group consisting of 6-butanoyloxy-3,7-dimethyl-8-methoxyisochroman, 3,7-dimethyl-8-methoxy-6-pentanoylisochroman, 3,7-dimethyl-6-hexanoyloxy-8-methoxyisochroman, 3,7-dimethyl-6-heptanoyloxy-8-methoxyisochroman, and 3,7-dimethyl-6-octanoyloxy-8-methoxyisochroman.

11. A compound selected from the group consisting of 3,7-dimethyl-6-methyoxy-8-propanoylisochroman, 8-butanoyloxy-3,7-dimethyl-6-methoxyisochroman, 3,7-dimethyl-8-pentanoyloxy-6-methoxyisochroman, and 3,7-dimethyl-8-hexanoyloxy-6-methoxyisochroman.

12. A compound selected from the group consisting of 3,7-dimethyl-8-ethoxy-6-methoxyisochroman, 3,7-dimethyl-6-methoxy-8-propoxyisochroman, 8-butoxy-3,7-dimethyl-6-methoxyisochroman, 3,7-dimethyl-8-hexanoxy-6-methoxyisochroman, 3,7-dimethyl-8-heptanoxy-6-methoxyisochroman, and 3,7-dimethyl-8-nonaoxy-6-methoxyisochroman.

13. An herbicidal composition consisting of
a compound of claim 9, and
a carrier;
wherein said compound is in an herbicidally effective amount.

14. An herbicidal composition consisting of
a compound of claim 10, and
a carrier;
wherein said compound is in an herbicidally effective amount.

15. An herbicidal composition consisting of
a compound of claim 11, and
a carrier;
wherein said compound is in an herbicidally effective amount.

16. An herbicidal composition consisting of
a compound of claim 12, and
a carrier;
wherein said compound is in an herbicidally effective amount.

* * * * *

UNITED STATES PATENT AND TRADEMARK OFFICE
CERTIFICATE OF CORRECTION

PATENT NO. : 5,922,889

DATED : July 13, 1999

INVENTOR(S) :. Cutler et al.

It is certified that error appears in the above-identified patent and that said Letters Patent is hereby corrected as shown below:

On the Title page, item [73] Assignee;
  Please add --University of Georgia Research Foundation,
     Athens, Georgia --.

Signed and Sealed this

Sixteenth Day of November, 1999

Attest:

Q. TODD DICKINSON

*Attesting Officer*     *Acting Commissioner of Patents and Trademarks*